(12) United States Patent
Kakuta et al.

(10) Patent No.: US 8,632,778 B2
(45) Date of Patent: Jan. 21, 2014

(54) STABILIZED ANTI-INTERLEUKIN-6 ANTIBODY-CONTAINING PREPARATIONS

(75) Inventors: Masaya Kakuta, Shizuoka (JP); Tadao Yamazaki, Shizuoka (JP); Akira Hayasaka, Shizuoka (JP); Yoshiki Hayashi, Shizuoka (JP); Tsutomu Arakawa, Thousand Oaks, CA (US)

(73) Assignee: Chugai Seiyaku Kabushiki Kaisha, Kita-Ku, Tokyo (JP)

( * ) Notice: Subject to any disclaimer, the term of this patent is extended or adjusted under 35 U.S.C. 154(b) by 497 days.

(21) Appl. No.: 10/380,102

(22) PCT Filed: Aug. 13, 2001

(86) PCT No.: PCT/JP01/06978
§ 371 (c)(1),
(2), (4) Date: Feb. 11, 2003

(87) PCT Pub. No.: WO02/13860
PCT Pub. Date: Feb. 21, 2002

(65) Prior Publication Data
US 2003/0190316 A1    Oct. 9, 2003

Related U.S. Application Data

(60) Provisional application No. 60/224,623, filed on Aug. 11, 2000, provisional application No. 60/224,834, filed on Aug. 11, 2000.

(51) Int. Cl.
*A61K 39/395* (2006.01)
*A61K 38/00* (2006.01)
*C07K 16/24* (2006.01)
*C12P 21/08* (2006.01)

(52) U.S. Cl.
USPC ............... 424/145.1; 530/388.23; 514/1.1

(58) Field of Classification Search
None
See application file for complete search history.

(56) References Cited

U.S. PATENT DOCUMENTS

| | | | | |
|---|---|---|---|---|
| 4,597,966 A | * | 7/1986 | Zolton et al. | 424/141.1 |
| 4,933,435 A | | 6/1990 | Ngo | |
| 4,992,419 A | | 2/1991 | Woog | 514/8 |
| 5,411,884 A | * | 5/1995 | Hellstrom et al. | 435/344.1 |

FOREIGN PATENT DOCUMENTS

| | | | |
|---|---|---|---|
| CA | 2052283 A1 | 3/1992 | |
| EP | 0 025 321 A2 | 3/1981 | ........... A61K 39/395 |
| EP | 0 025 719 A2 | 3/1981 | ........... A61K 39/395 |
| EP | 0 187 712 A2 | 7/1986 | ........... A61K 39/395 |
| EP | 0409607 A2 | 1/1991 | |
| EP | 0 420 649 A2 | 4/1991 | ............... A61K 9/00 |
| EP | 0597101 A1 | 5/1994 | |
| EP | 0628639 A1 | 12/1994 | |
| JP | 61159167 | 7/1986 | |
| JP | 64-71818 | 3/1989 | ............. A61K 37/02 |
| JP | H02290900 | 11/1990 | |
| JP | 3-139293 A | 6/1991 | |
| JP | H05199888 | 8/1993 | |
| JP | 08099902 | 4/1996 | |
| JP | 11510170 | 9/1999 | |
| JP | 2002504907 A | 2/2002 | |
| WO | 92/19759 A1 | 11/1992 | |
| WO | 9704801 A1 | 2/1997 | |
| WO | WO 97/04801 | * 2/1997 | |
| WO | WO 98/22136 | 5/1998 | |
| WO | 9856418 A1 | 12/1998 | |
| WO | 0045841 A2 | 8/2000 | |

OTHER PUBLICATIONS

Tsunenari T, et al. Therapeutic potential of humanized anti-interleukin-6 receptor antibody: antitumor activity in xenograft model of multiple myeloma. 1996. Anticancer Research. vol. 16, p. 2537-2544.*
T. Osterberg et al., "Physical state of 1-histidine after freeze-drying and long-term storage", 8 Eur. J. Pharmaceut. Sci. 301-308, 1999.
S. Sweetana et al., "Solubility principles and practices for parenteral drug dosage form development", 50(5) PDA J. Pharmaceut. Sci. Technol. 330-42,1996.
W. Wang, "Instability, stabilization, and formulation of liquid protein pharmaceuticals", 185 Int'l J. Pharmaceut. 129-88, 1999.
Supplemental European Search Report of related European Patent Application No. EP 01 95 5698, completed Sep. 8, 2008, mailed Sep. 15, 2008.

* cited by examiner

*Primary Examiner* — Robert Landsman
*Assistant Examiner* — Bruce D Hissong
(74) *Attorney, Agent, or Firm* — Browdy and Neimark, PLLC

(57) ABSTRACT

The present invention provides stabilized preparations containing an antibody in a glycine buffer and/or a histidine buffer and also provides processes for preparing a protein-containing stabilized preparation, comprising adjusting the pH with a basic amino acid or a basic amino acid derivative or a salt thereof.

9 Claims, 14 Drawing Sheets

STABILIZED ANTI-INTERLEUKIN-6 ANTIBODY-CONTAINING PREPARATIONS

This application is a 371 of PCT/JP01/06978, filed Aug. 13, 2001, which claims benefit of U.S. Provisional Applications 60/224,623 and 60/224,834, both filed Aug. 11, 2000.

FIELD OF THE INVENTION

The present invention relates to antibody-containing preparations, particularly stabilized antibody-containing preparations with low loss of active ingredients even after long-term storage. The present invention also relates to processes for preparing protein-containing stabilized preparations, comprising adjusting the pH with a basic amino acid or a basic amino acid derivative or a salt thereof.

BACKGROUND ART

A number of injectable protein-containing preparations are supplied to the market, in which various measures are taken to provide stabilized protein-containing preparations with low loss of active ingredients even after long-term storage. Protein-containing preparations are prepared by dissolving active ingredients and various additives such as diluents, solubilizers, excipients, soothing agents, buffering agents, sulfur-containing reducing agents, antioxidants, stabilizers, surfactants, etc. in a buffer.

A problem generally associated with the storage of proteins stored as concentrated solutions is their deterioration as exemplified by the formation of insoluble aggregates and that must be prevented.

For example, antibodies such as immunoglobulins, monoclonal antibodies and humanized antibodies are unstable proteins liable to physical or chemical changes such as association or aggregation under stresses of filtration, concentration and heating for removing viruses during the purification process.

A conventional method widely used for inhibiting deterioration of proteins to stably store them is stabilization by freeze-drying. However, it was necessary to add some agent for protecting against freezing to avoid denaturation or chemical changes that might be caused by mechanical stresses during freezing and freeze-drying.

A stabilization effect was found by adding as a stabilizer for inhibiting chemical or physical changes, polymers or polyols including proteins such as human serum albumin or purified gelatin or oligomers such as amino acids and surfactants. However, the addition of biopolymers such as proteins as stabilizers had problems such as the necessity of a very complex step for removing contaminants such as viruses derived from the stabilizers. Moreover, heat treatments for inactivating viruses sometimes caused problems such as association or aggregation due to heat stresses.

Interleukin-6 (IL-6) receptor is a ligand-binding protein having a molecular weight of about 80 KD to which IL-6 binds. Anti-IL-6 receptor antibodies were found to have a therapeutic effect on various IL-6-mediated diseases such as immune disorders, inflammatory diseases or lymphocyte tumors by blocking IL-6 signal transduction in immature myeloma cells to inhibit biological activities of IL-6 (Tsunenari, T. et al., Blood, 90:2437, 1997; Tsunenari T. et al., Anticancer Res. 16:2537, 1996). We also found that anti-IL-6 receptor antibodies have a therapeutic effect on immature myeloma cells (JP-A-8-099902).

We succeeded in the mass production of a reshaped humanized antibody hPM-1 as one of such anti-IL-6 receptor antibodies, and have tried to formulate this purified anti-IL-6 receptor antibody into pharmaceutical preparations.

Similarly to other protein preparations, an important factor for formulation of anti-IL-6R antibodies is chemical and physical stability. Especially, humanized anti-IL-6 receptor antibodies are unstable proteins liable to physical or chemical changes such as association or aggregation under stresses of filtration, concentration and heating for virus elimination during the purification process.

Thus, there is a demand for the development and commercialization of preparations containing an antibody, especially a humanized anti-IL-6 receptor antibody, which are stable even after long-term storage.

As for various physiologically active proteins, it is also necessary to establish preparation conditions and storage conditions for maintaining their structures and activities in order to supply them as pharmaceuticals in constant amount and with high quality. Especially, it would be desirable to develop a method for inhibiting formation of insoluble aggregates in protein solutions.

DISCLOSURE OF THE INVENTION

As a result of careful studies to achieve the above objects, we accomplished the present invention on the basis of the finding that heat-induced aggregation is controlled by formulating a humanized anti-interleukin-6 receptor antibody in a glycine buffer and/or histidine buffer and that such formulations are further stabilized by adding glycine and/or sucrose.

We also accomplished the present invention on the basis of the finding that aggregation can be reduced and stabilization effect can be increased by adjusting the pH with a basic amino acid or a basic amino acid derivative or a salt thereof.

Accordingly, the present invention provides:

(1) a stabilized preparation containing an antibody in a glycine buffer and/or a histidine buffer;

(2) the stabilized preparation as defined in (1) above wherein the antibody is a chimeric antibody or a humanized antibody;

(3) the stabilized preparation as defined in (1) or (2) above wherein the antibody is an anti-interleukin-6 receptor antibody;

(4) the stabilized preparation as defined in (3) above wherein the anti-interleukin-6 receptor antibody is a humanized anti-interleukin-6 receptor antibody;

(5) the stabilized preparation as defined in (1) above wherein the concentration of the glycine buffer and/or histidine buffer is 5 mM-200 mM;

(6) the stabilized preparation as defined in any one of (1) to (5) above which contains glycine and/or sucrose as an isotonizing agent;

(7) the stabilized preparation as defined in (6) above containing 0.05-1 M glycine and/or sucrose;

(8) the stabilized preparation as defined in any one of (1) to (7) above, which does not contain NaCl as an isotonizing agent;

(9) a stabilized preparation containing glycine and/or sucrose as an isotonizing agent as well as a humanized anti-interleukin-6 receptor antibody in a glycine buffer and/or a histidine buffer;

(10) the stabilized preparation as defined in any one of (1) to (9) above having a pH of 5-8;

(11) a method for stabilizing an antibody preparation, comprising incorporating an antibody in a glycine buffer and/or histidine buffer;

(12) the method as defined in (11) above, comprising incorporating glycine and/or sucrose as an isotonizing agent;

(13) a method for stabilizing an anti-interleukin-6 receptor antibody preparation, comprising incorporating glycine and/or sucrose as an isotonizing agent as well as a humanized anti-interleukin-6 receptor antibody in a glycine buffer and/or a histidine buffer;

(14) a process for preparing a stabilized preparation containing a physiologically active protein, comprising adjusting the pH with a basic amino acid or a basic amino acid derivative or a salt thereof;

(15) the process as defined in (14) above wherein the basic amino acid is one or more members selected from histidine, arginine and lysine;

(16) the process as defined in (15) above wherein the basic amino acid is histidine;

(17) the process as defined in any one of (14) to (16) above wherein the physiologically active protein is a recombinant protein;

(18) the process as defined in any one of (14) to (17) above wherein the physiologically active protein is an antibody;

(19) the process as defined in (18) above wherein the antibody is a chimerized antibody or a humanized antibody;

(20) the process as defined in (18) or (19) above wherein the antibody is an anti-interleukin-6 receptor antibody;

(21) the process as defined in (20) above wherein the anti-interleukin-6 receptor antibody is a humanized anti-interleukin-6 receptor antibody;

(22) a stabilized preparation containing an antibody in a histidine buffer and having a pH of 5-7.5;

(23) the stabilized preparation as defined in (22) above wherein the antibody is an anti-interleukin-6 receptor antibody;

(24) the stabilized preparation as defined in (23) above wherein the anti-interleukin-6 receptor antibody is a humanized anti-interleukin-6 receptor antibody;

(25) the stabilized preparation as defined in (24) above having a pH of 5.5-6.2;

(26) the stabilized preparation as defined in (25) above wherein the concentration of histidine is 1-50 mM;

(27) the stabilized preparation as defined in (26) above wherein the concentration of histidine is 3-20 mM;

(28) the stabilized preparation as defined in (27) above wherein the concentration of histidine is 5-10 mM;

(29) the stabilized preparation as defined in (24) above having a pH of 6.2-7.5;

(30) the stabilized preparation as defined in (29) above wherein the concentration of histidine is 5-200 mM;

(31) the stabilized preparation as defined in (30) above wherein the concentration of histidine is 10-150 mM;

(32) the stabilized preparation as defined in (31) above wherein the concentration of histidine is 25-100 mM;

(33) the stabilized preparation as defined in any one of (22) to (32) above further containing glycine and/or sucrose;

(34) the stabilized preparation as defined in (33) above containing 0.05-1 M glycine and/or sucrose; and

(35) the stabilized preparation as defined in any one of (22) to (34) above, which has its pH adjusted with a basic amino acid or a basic amino acid derivative or a salt thereof.

THE MOST PREFERRED EMBODIMENTS OF THE INVENTION

Figure 1:
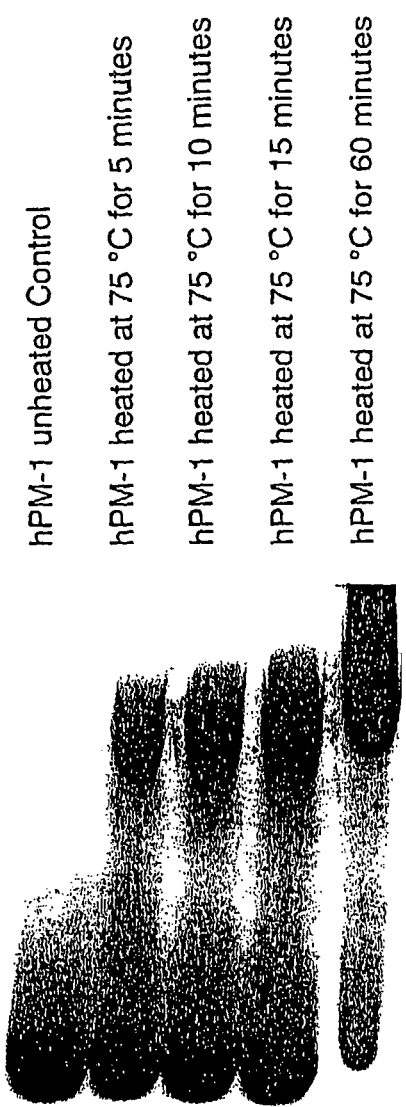
FIG. 1 shows the results of native gel electrophoresis showing aggregation when antibody hPM-1 dissolved in 19 mM sodium phosphate, 0.2 M NaCl, pH 6.5 was heat-treated at 75° C. (electrophoretogram).

Antibodies used in stabilized preparations of the present invention are preferably monoclonal antibodies, which may be prepared by any process. Monoclonal antibodies can be basically constructed by known techniques as follows. A suitable host is immunized with an immunizing antigen according to a standard immunization technique, and the resulting immunized cells are fused to known parent cells by a standard cell fusion technique, and then the fused cells are screened for monoclonal antibody-producing cells by a standard screening method.

Antibodies contained in stabilized preparations of the present invention include, but not limited to, anti-IL-6 receptor antibodies, anti-HM1.24 antigen monoclonal antibodies, anti-parathyroid hormone related peptide antibodies (anti-PTHrP antibodies), anti-tissue factor antibodies, etc. For example, anti-IL-6 receptor antibodies include PM-1 (Hirata et al., J. Immunol. 143:2900-2906, 1989), AUK12-20, AUK64-7 or AUK146-15 (International Publication No. WO92/19759).

Monoclonal antibodies are not limited to those produced by hybridomas, but also include chimeric antibodies obtained by artificial modifications to lower heteroantigenicity to human or for other purposes. Reshaped humanized antibodies can also be used in the present invention, which are obtained by replacing the complementarity-determining regions of a human antibody by the complementarity-determining regions of a non-human mammalian antibody such as a mouse antibody by standard gene recombination techniques also known. These known techniques can be used to obtain reshaped humanized antibodies.

If necessary, reshaped humanized antibodies may have some amino acid changes in the framework regions (FRs) of the variable regions so that the complementarity-determining regions form an appropriate antigen-binding site (Sato et al., Cancer Res. 53:1-6, 1993). Such reshaped humanized antibodies are preferably exemplified by humanized anti-IL-6 receptor antibodies (hPM-1) (see International Publication No. WO92/19759). Other preferred antibodies for use in the present invention include humanized anti-HM1.24 antigen monoclonal antibodies (see International Publication No. WO98/14580), humanized anti-parathyroid hormone related peptide antibodies (anti-PTHrP antibodies) (see International Publication No. WO98/13388), humanized anti-tissue factor antibodies (see International Publication No. WO99/51743), etc.

Human antibodies constructed with transgenic animals or the like are also preferred.

Antibodies also include reshaped antibody fragments such as Fab and (Fab')$_2$ and monovalent or multivalent single-chain antibodies (scFvs).

Physiologically active protein-containing samples or antibody-containing samples herein may be samples containing any protein or antibody irrespective of whether it is a biological protein or antibody or a recombinant protein or antibody, preferably culture media of mammalian cells such as CHO cells containing a physiologically active protein or antibody obtained by cultivation or those media having undergone some treatment such as partial purification.

We tested heat stability of antibody hPM-1 dissolved in 19 mM sodium phosphate, 0.2 M NaCl, pH 6.5 to find that aggregation scarcely occurred even after extended incubation at 70° C. or less. Then, aggregates were formed when antibody hPM-1 was heat-treated at 75° C. This result shows that aggregation is induced in antibody hPM-1 only after thermal transition characterized by a fusion point of 72° C. has been passed. As the incubation period increased, the intensity of the aggregate band increased and the monomer content was almost lost after 60 minutes. These aggregates seemed to be non-covalent because they dissociated in the presence of sodium dodecyl sulfate.

After examinations of various factors contributing to the inhibition of this heat-induced aggregation, we found that aggregation can be controlled by dissolving a humanized anti-IL-6 receptor antibody in a glycine buffer and/or a histidine buffer.

Therefore, stabilized preparations of the present invention can be prepared by dissolving an antibody in a glycine buffer and/or a histidine buffer.

The glycine buffer or histidine buffer has a concentration of 5-200 mM, preferably 5-50 mM, more preferably 5-20 mM. The glycine buffer and histidine buffer may be used alone or in combination at a total concentration within the above range.

Stabilized preparations of the present invention can be more stable preparations with less aggregation by adding glycine and/or sucrose as an isotonizing agent. The amount of glycine and/or sucrose to be added is 0.05-1 M. Preparations of the present invention are preferably free from NaCl because the aggregation-reducing effect of glycine and/or sucrose is lowered by adding NaCl.

Stabilized preparations of the present invention preferably have a pH of 5-8.

We also examined various factors contributing to the inhibition of aggregation to find that aggregation is reduced and stabilization effect is increased by adjusting the pH with a basic amino acid or a basic amino acid derivative or a salt thereof rather than NaOH as used in conventional methods.

Accordingly, the present invention provides processes for preparing a protein-containing stabilized preparation, comprising adjusting the pH with a basic amino acid or a basic amino acid derivative or a salt thereof.

Processes for preparing a physiologically active protein-containing stabilized preparation of the present invention are useful for not only antibody-containing preparations as described above but also other physiologically active protein-containing preparations. For example, physiologically active proteins include, but not limited to, hematopoietic factors such as granulocyte colony-stimulating factor (G-CSF), granulocyte macrophage colony-stimulating factor (GM-CSF), erythropoietin (EPO) and thrombopoietin; cytokines such as interferon, IL-1 and IL-6; monoclonal antibodies; tissue plasminogen activator (TPA); urokinase; serum albumin; blood coagulation factor VIII; leptin; insulin; and stem cell growth factor (SCF). Preferred proteins are hematopoietic factors such as EPO, G-CSF and thrombopoietin and monoclonal antibodies, more preferably EPO, G-CSF and monoclonal antibodies.

Physiologically active proteins used as active ingredients in the present invention may be derived from natural sources or preferably genetically engineered so far as they have substantially the same biological activities as those of physiologically active proteins of mammals, especially human. Genetically engineered proteins may have the same amino acid sequences as those of natural proteins or may contain deletion, substitution or addition of one or more amino acids in the amino acid sequences while maintaining the biological activities. Physiologically active proteins also include those chemically modified with PEG or the like.

Physiologically active proteins used as active ingredients in the present invention include, for example, proteins having a sugar chain. The sugar chain may be derived from any source, but preferably those for glycosylation in mammalian cells. Mammalian cells include, for example, Chinese hamster ovary (CHO) cells, BHK cells, COS cells, human-derived cells, etc., among which CHO cells are most preferred.

When the physiologically active protein used as an active ingredient in the present invention is EPO, EPO may be prepared by any process, e.g. it may be extracted from human urine and isolated and purified by various techniques or may be produced by genetic engineering techniques (see JP-A-61-012288, for example) in Chinese hamster ovary (CHO) cells, BHK cells, COS cells, human-derived cells or the like and then extracted and isolated and purified by various techniques. EPO chemically modified with PEG or the like is also included (see International Publication No. WO90/12874). EPO having no sugar chain and chemically modified with PEG or the like is also included. EPO analogs are also included, in which EPO has been modified to increase the number of one or more glycosylation sites at the N-linked carbohydrate chain binding site or O-linked carbohydrate binding site in the amino acid sequence of EPO (see JP-A-8-151398 and JP-A-8-506023, for example). Moreover, the amount of sugar chains may be increased by increasing the content of sialic acid or the like without changing the number of sugar chain-binding sites.

When the physiologically active protein used as an active ingredient in the present invention is G-CSF, any of the highly purified human G-CSFs can be used. G-CSF in the present invention may be prepared by any process, e.g., they may be extracted from cultures of a human tumor cell line and isolated and purified by various techniques or may be produced by genetic engineering techniques in bacterial cells such as *E. coli*; yeast cells; animal culture cells such as Chinese hamster ovary (CHO), C127 or COS cells and then extracted and isolated and purified by various techniques. G-CSF is preferably produced by genetic recombination in *E. coli*, yeast or CHO cells, most preferably by genetic recombination in CHO cells. G-CSF chemically modified with PEG or the like is also included (see International Publication No. WO90/12874).

The basic amino acid used for adjusting the pH is preferably one or more members selected from histidine, arginine and lysine, most preferably histidine.

Basic amino acids or basic amino acid derivatives or salts thereof include free basic amino acids or basic amino acid derivatives and their salts such as sodium salts, potassium salts or hydrochlorides. Basic amino acids or basic amino acid derivatives or salts thereof used in processes and preparations of the present invention may be in D-, L- or DL-configuration, more preferably L-configuration. Basic amino acid derivatives include amino acid nitro compounds, amino alcohols, dipeptides or the like. For example, histidine derivatives include derivatives described in JP-A-11-315031, i.e. histidine methyl ester, His-Gly, His-Ala, His-Leu, His-Lys, His-Phe, imidazole, histamine or imidazole-4-acetic acid.

In processes of the present invention, the pH is preferably adjusted to 5-7.5 with a basic amino acid or a basic amino acid derivative or a salt thereof, preferably one or more members selected from histidine, arginine, lysine or derivatives or salts thereof, most preferably histidine or a derivative thereof or a salt thereof. Most preferably, the pH is adjusted with histidine.

In a preferred embodiment of a process of the present invention, a preparation containing an antibody in a histidine buffer is pH-adjusted with a basic amino acid or a basic amino acid derivative or a salt thereof. For example, aggregation can be reduced when a humanized anti-interleukin-6 receptor antibody is contained in a histidine buffer rather than conventional phosphate buffers. However, other buffers can also be used.

A correlation exists between the pH of preparations and preferred histidine concentrations in buffers. When the pH of preparations is 5.5-6.2, preferably 5.7-6.2, stabilization effect is especially remarkable at a histidine concentration of 1-50 mM, preferably 3-20 mM, more preferably 5-10 mM. When the pH of preparations is 6.2-7.5, preferably 6.3-7.0, stabilization effect is remarkable at a histidine concentration of 5-200 mM, preferably 10-150 mM, more preferably 25-100 mM.

Stabilized preparations of the present invention can be more stable preparations with less aggregation by further adding glycine and/or sucrose. The amount of glycine and/or sucrose to be added is preferably 0.05-1 M.

Preparations of the present invention may further contain isotonizing agents, e.g., polyethylene glycol; and sugars such as dextran, mannitol, sorbitol, inositol, glucose, fructose, lactose, xylose, mannose, maltose and raffinose.

Stabilized preparations of the present invention may further contain surfactants. Typical examples of surfactants include:

nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18;

anionic surfactants, e.g., alkyl sulfates having a C10-C18 alkyl group such as sodium cetyl sulfate, sodium lauryl sulfate, sodium oleyl sulfate; polyoxyethylene alkyl ether sulfates having an average ethylene oxide mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids. One or more of these surfactants may be added in combination to preparations of the present invention.

Stabilized preparations of the present invention may further contain diluents, solubilizing agents, excipients, pH-modifiers, soothing agents, buffering agents, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate. Other components commonly added may also be contained, e.g., inorganic salts such as sodium chloride, potassium chloride, calcium chloride, sodium phosphate, potassium phosphate and sodium bicarbonate; and organic salts such as sodium citrate, potassium citrate and sodium acetate.

Stabilized preparations of the present invention are normally administered via parenteral routes such as injection (e.g. subcutaneous, intravenous, intramuscular or intraperitoneal injection) or percutaneous, mucosal, nasal or pulmonary administration, but may also be orally administered.

Stabilized preparations of the present invention may also be in the form of solution formulations or freeze-dried formulations to be reconstituted in solution before use. Suitable excipients for freeze-drying include sugar alcohols or sugars such as mannitol or glucose.

The amount of antibodies contained in preparations of the present invention depends on the type of the disease to be treated, the severity of the disease, the age of the patient and other factors, but generally ranges from 0.1-200 mg/ml, preferably 1-120 mg/ml expressed as a final concentration.

INDUSTRIAL APPLICABILITY

As shown in the examples below, it was demonstrated that heat-induced aggregation can be controlled with stabilized preparations of the present invention formulated in a glycine buffer and/or a histidine buffer and that aggregation can be further reduced by adding glycine and/or sucrose.

According to processes for preparing a stabilized preparation containing a physiologically active protein of the present invention, heat-induced aggregation can be controlled to provide a stable preparation by adjusting the pH with a basic amino acid or a basic amino acid derivative or a salt thereof.

The following examples further illustrate the present invention without, however, limiting the scope of the invention thereto. Various changes and modifications can be made by those skilled in the art on the basis of the description of the invention, and such changes and modifications are also included in the present invention.

EXAMPLES

Test Methods (1) Materials

Antibody hPM-1 was used as a humanized anti-IL-6 receptor antibody. Antibody hPM-1 is a humanized antibody prepared according to the protocol described in Reference example 2 of JP-A-8-099902 using the human elongation factor Iα promoter described in Example 10 of International Publication No. WO92/19759. Antibody hPM-1 was purified through a protein A column and stored in 19 mM sodium phosphate, 0.2 M NaCl, pH 6.5.

(2) Determination of Protein Concentrations

Protein concentrations were calculated from the absorbances measured at 280 nm with a spectrophotometer (DU-600, Beckman-Coulter) using extinction coefficients per mg/ml (calculated from the amino acid sequence).

(3) Sedimentation Velocity

Sedimentation velocity determined by analytical ultracentrifugation is an excellent tool for detecting minor changes in protein aggregation. This method can detect aggregation on the level of about 1% by weight.

All samples were diluted with various formulated buffers to about 0.5 mg/ml immediately before analysis and scanned for very large aggregates sedimented by centrifugation at a low rotor speed of 3,000 rpm using a Beckman XLA analytical ultracentrifuge at 20° C. Then, the monomer and small oligomers were sedimented at a rotor speed of 45,000 rpm.

Data were analyzed by the program DCDT+ developed by John Philo using the dc/dt method (Stafford, Anal. Biochem. 203:295-230, 1992). In some cases, the program SVEDBERG (also developed by John Philo) was used.

(4) Native Gel Electrophoresis

Protein aggregation was analyzed by native gel electrophoresis in the absence of SDS. In this method, the mobility of proteins depends on both hydrodynamic size and charge state. Native gel electrophoresis allows non-covalent protein aggregates to be detected in the absence of SDS. We developed a protocol for native gel analysis of antibody hPM-1, because antibody hPM-1 is a basic protein for which the ordinary polarity in normal Tris-glycine buffer systems or SDS gel electrophoresis cannot be applied.

Native gel electrophoresis was performed on a 7% Novex NuPAGE Tris-acetate gel (purchased from Novex). The electrode buffer used was 80 mM β-alanine/40 mM AcOH, pH 4.4 or 30 mM histidine/30 mM MES, pH 6.1. Antibody hPM-1 was positively charged at pH 6.1, and subjected to electrophoresis in a direction from the anode to cathode. Samples were mixed with a 5-fold excess of the electrode buffer containing sucrose and methyl green.

Example 1

Heat Stability of Antibody hPM-1

Antibody hPM-1 dissolved in 19 mM sodium phosphate, 0.2 M NaCl, pH 6.5 was tested for heat stability. FIG. 1 shows the results of native gel electrophoresis before and after heat treatment at 75° C. for 5-60 minutes.

In FIG. 1, a single band appears before heat treatment to show that the purified protein is very homogeneous in charge state and size. Sedimentation velocity of the same sample was constant to show it is a monomer species. After heating at 75° C. for 5 minutes, a band corresponding to aggregates was observed. As the incubation period increased, the intensity of the aggregate band increased and the monomer content was almost lost after 60 minutes. These aggregates seemed to be non-covalent because they dissociated in the presence of sodium dodecyl sulfate.

Example 2

Effect of the Type of Buffer on Aggregation

Five buffers (all 19 mM) were used to examine their effect on aggregation. The pHs of samples prepared by dissolving an antibody hPM-1 preparation in these buffers (at a concentration of about 1 mg/ml) are as follows.

1) sodium phosphate (pH 6.8)
2) histidine-HCl (pH 7.1)
3) sodium citrate (pH 6.7)
4) Tris-HCl (pH 7.2)
5) glycine (pH 7.6).

Figure 2:
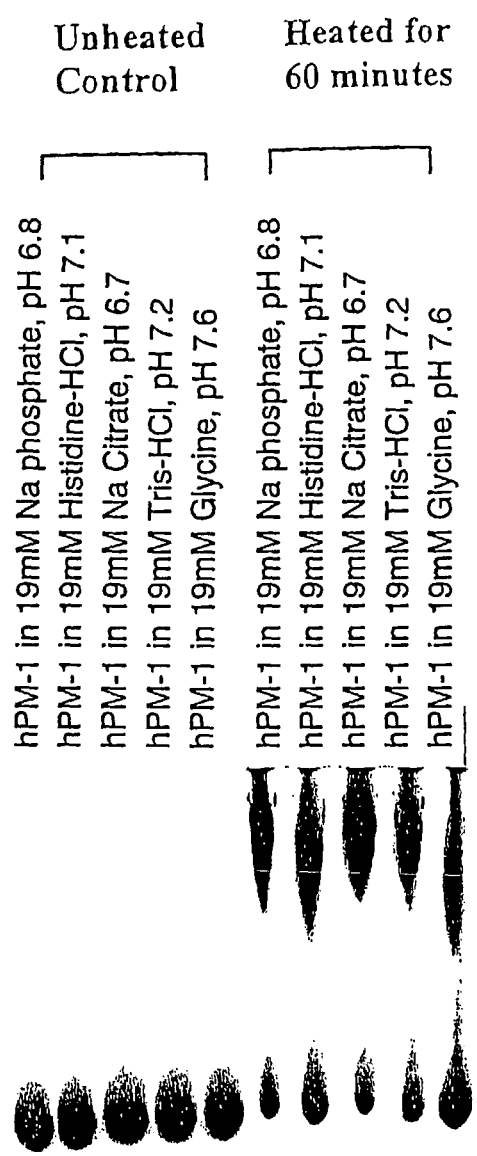
FIG. 2 shows the results of native gel electrophoresis showing the effect of the type of buffer on aggregation (electrophoretogram).

These samples were heated at 75° C. for 60 minutes and subjected to native gel analysis. FIG. 2 shows the results before and after heating. The monomer content was the highest to give the smallest amount of aggregation in glycine and it decreased in the order of histidine-HCl, Tris-HCl, sodium phosphate and sodium citrate. Very few aggregates were observed in glycine.

Figure 3:
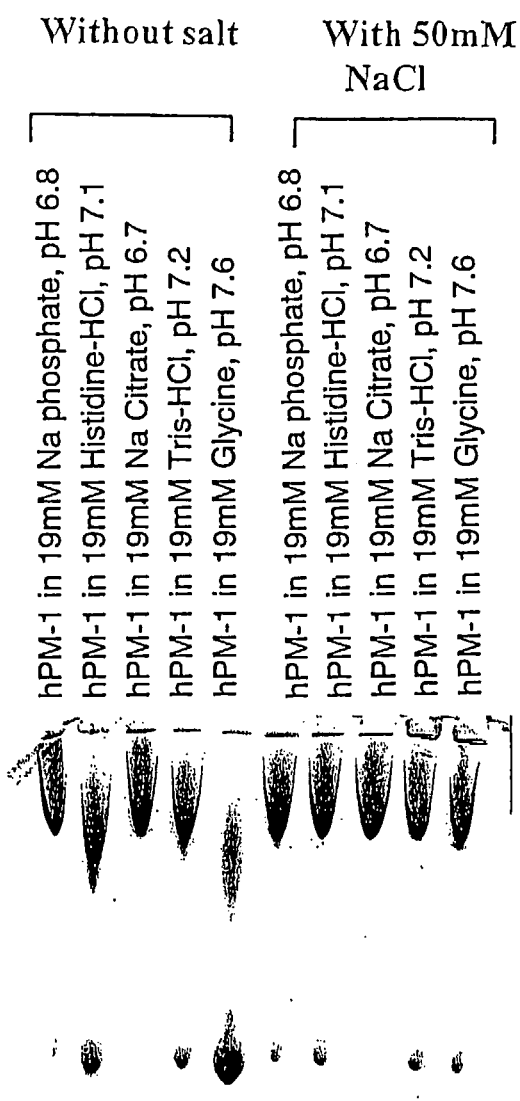
FIG. 3 shows the results of native gel electrophoresis showing the effect of adding 50 mM NaCl into buffers and heating on aggregation (electrophoretogram).

When 50 mM NaCl was added to these buffers, aggregation after heating greatly increased in any buffers (FIG. 3).

Example 3

Effect of the Type of Buffer on Sedimentation Distribution

Figure 4:
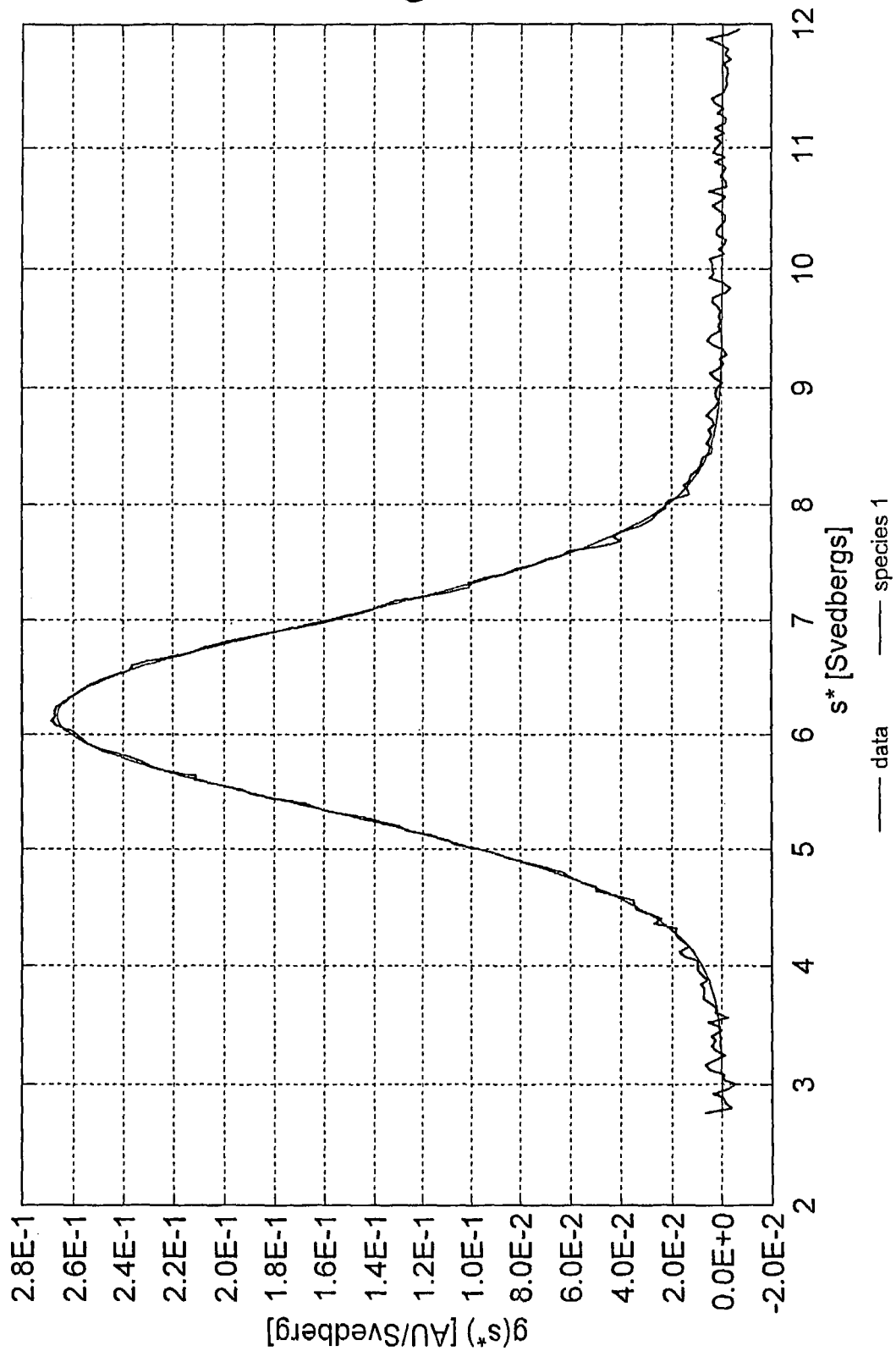
FIG. 4 shows the sedimentation coefficient distribution g(s*), obtained by DCDT and analysis of a control antibody hPM-1 in 19 mM sodium phosphate, 0.2 M NaCl.
Figure 5:
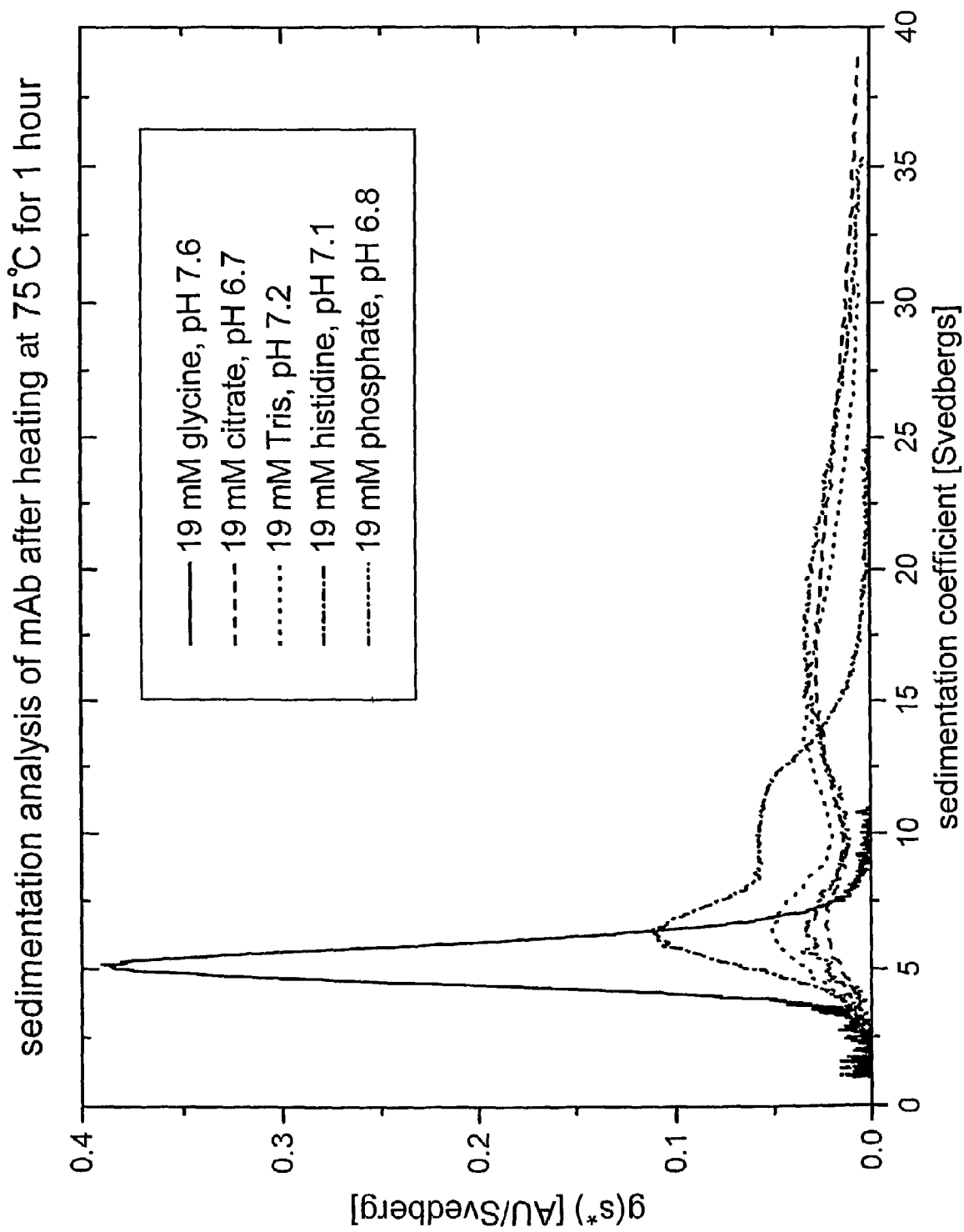
FIG. 5 shows the sedimentation coefficient distribution g(s*), showing the effect of the type of buffer on aggregation.

In order to examine the nature of heat-induced aggregation in these buffers, a sedimentation test was then performed. FIG. 4 shows the sedimentation coefficient distribution g(s*) obtained from the dc/dt analysis of a control antibody hPM-1 in 19 mM sodium phosphate, 0.2 M NaCl. This sample is shown to be a single species having a sedimentation coefficient of about 6.2 svedbergs (S). FIG. 5 shows the sedimentation profile of an antibody hPM-1-containing preparation sample dissolved in five buffers shown in Example 2 and heated at 75° C. for 60 minutes. Considerable aggregation and monomer species loss were observed in the other buffers than 19 mM glycine, pH 7.6. Monomer loss was the greatest in sodium citrate, followed by sodium phosphate, Tris-HCl, histidine-HCl and glycine in descending order. Broad distribution representing the existence of aggregates was observed in phosphate, citrate and Tris, which extended to 40 S or more and had a peak at about 15-18 S. Aggregates observed in histidine were not observed at about 25 S or more and had a peak at about 10 S. These results agree with the results of native gel analysis on the preparations after heat treatment described in Example 2.

Example 4

Effect of Glycine and Sucrose

Figure 6:
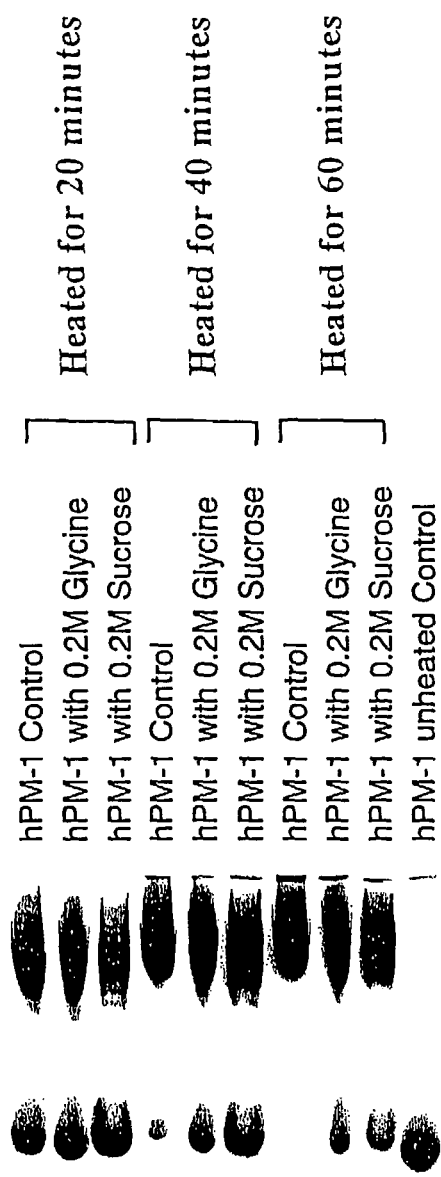
FIG. 6 shows the results of native gel electrophoresis showing the effect of glycine and sucrose on aggregation (electrophoretogram).

This example relates to evaluation of the effect of glycine or sucrose on aggregation as used in place of NaCl. Samples of antibody hPM-1 dissolved in 19 mM sodium phosphate, 0.2 M NaCl, pH 6.5 were dialyzed against 19 mM sodium phosphate, pH 6.5 containing 0.2 M glycine or 0.2 M sucrose. These samples were heated at 75° C. for 20-60 minutes in parallel. FIG. 6 shows the results of native gel electrophoresis. Comparing monomer bands, the monomer content was lower in 19 mM sodium phosphate, 0.2 M NaCl after heating for 20 minutes. This difference became more significant when the incubation period was extended to 40 and 60 minutes. Sucrose was more effective than glycine in reducing aggregation of antibody hPM-1 induced by heat treatment. Thus, NaCl showed a negative effect on the prevention of aggregation as it did in Example 2.

Example 5

Native Gel Analysis of Antibody hPM-1 Samples Before and After Heating

Figure 7:
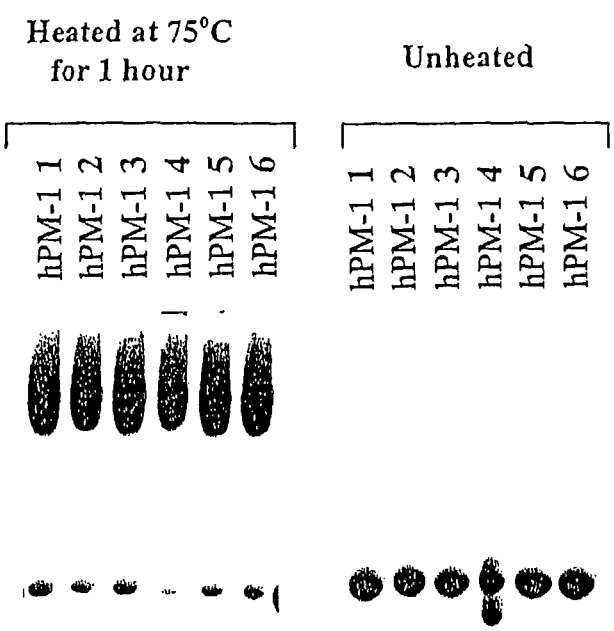
FIG. 7 shows the results of native gel analysis of six samples (samples 1 to 6) before and after heating (electrophoretogram).

Six samples (samples 1 to 6) of said antibody hPM-1 preparation stored in 19 mM sodium phosphate, 0.2 M NaCl, pH 6.5 were subjected to native gel analysis. The results of about 28 μg samples on the gel are shown in the right lane of FIG. 7.

Said six samples were diluted in 20 mM sodium phosphate, 0.2 M NaCl, pH 6.5 to prepare an antibody hPM-1 solution at a concentration of about 2 mg/ml, which was dialyzed against the buffer. After dialysis, the protein concentrations were spectrophotometrically determined at an extinction coefficient of 1.401 with the results below.

Sample 1: 1.87 mg/ml
Sample 2: 1.77 mg/ml
Sample 3: 1.89 mg/ml
Sample 4: 1.89 mg/ml
Sample 5: 1.87 mg/ml
Sample 6: 1.85 mg/ml.

These samples were subjected to native gel analysis. The results were the same as shown in the right lane of FIG. 7, confirming that aggregation was not influenced by dilution and dialysis.

Then, these samples were heated at 75° C. for one hour and subjected to native gel analysis in the same manner (except that 49 μg samples were used). The results are shown in the left lane of FIG. 7. The antibody hPM-1 monomer content remarkably decreased in all the samples to show that aggregates were formed.

Example 6

Effect of the Type and pH of Buffer on Aggregation

Sample 6 was diluted in the five buffers below to prepare antibody hPM-1 solutions at a concentration of about 2 mg/ml.

Sample 6-1: 5 mM phosphate/Na, pH 6.5 [5 mM sodium phosphate (monobasic) adjusted to pH 6.5 with concentrated NaOH];

Sample 6-2: 5 mM phosphate/His, pH 6.0 [5 mM sodium phosphate (monobasic) adjusted to pH 6.0 with concentrated histidine (base) to a final histidine concentration of 1 mM];

Sample 6-3: 5 mM phosphate/His, pH 6.5 [5 mM sodium phosphate (monobasic) adjusted to pH 6.5 with concentrated histidine (base) to a final histidine concentration of 6.6 mM];

Sample 6-4: 5 mM phosphate/Na+20 mM His/HCl, pH 6.5 [10 mM phosphate, pH 6.5 mixed with an equal amount of 40 mM His/HCl, pH 6.5]; and Sample 6-5: 5 mM phosphate/Na, pH 6.0 [5 mM sodium phosphate (monobasic) adjusted to pH 6.0 with concentrated NaOH].

These samples were dialyzed against the respective buffers shown above. After dialysis, the protein concentrations were determined with the results below.

Sample 6-1: 1.80 mg/ml
Sample 6-2: 1.75 mg/ml
Sample 6-3: 1.82 mg/ml
Sample 6-4: 1.84 mg/ml
Sample 6-5: 1.68 mg/ml.

These samples were subjected to native gel analysis before and after heat treatment at 75° C. for 1 hour.

Figure 8:
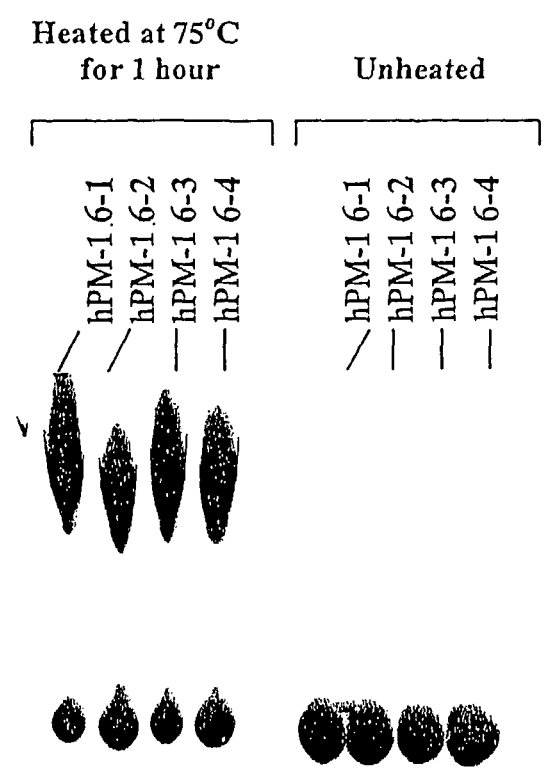
FIG. 8 shows the results of native gel analysis of samples 6-1, 6-2, 6-3 and 6-4 before and after heating (electrophoretogram).

FIG. 8 shows the analytical results of samples 6-1, 6-2, 6-3 and 6-4. Aggregation was the least in sample 6-2 followed by sample 6-4. This showed that pH 6.0 gave better results than pH 6.5 and that pH adjustment with histidine had a stabilization effect.

Figure 9:
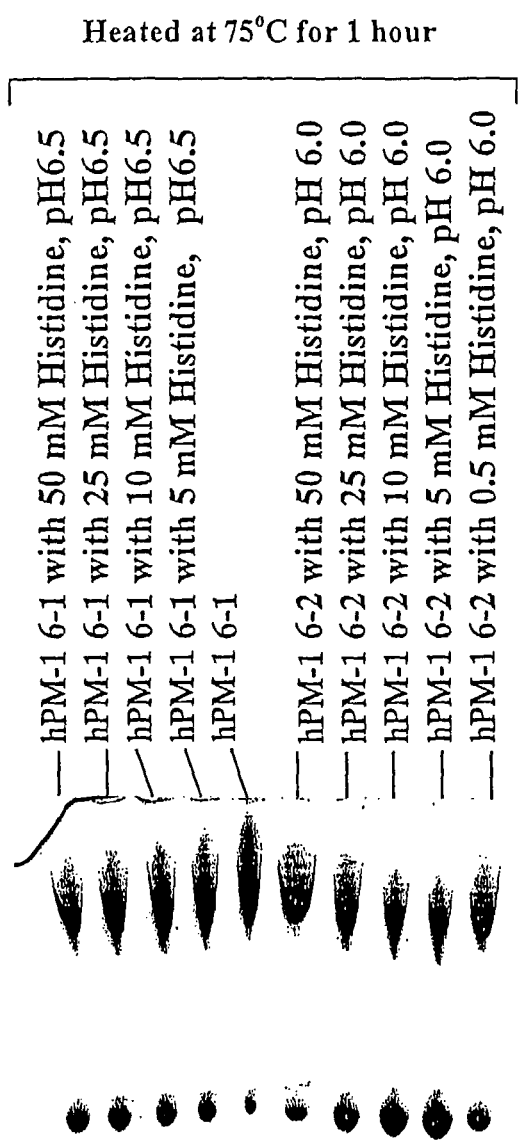
FIG. 9 shows the results of native gel analysis in which samples 6-1 and 6-2 were compared at various histidine concentrations (electrophoretogram).

FIG. 9 shows the results of comparison of samples 6-1 and 6-2 at various histidine concentrations. The samples were prepared by mixing sample 6-1 or 6-2 with a 0.25 M histidine solution (mixed with the corresponding buffer to adjust pH). Less aggregates were formed at pH 6.0 (sample 6-2) than pH 6.5 (sample 6-1), showing that the effect of histidine varies with pH.

The stabilization effect of histidine was considerable at a concentration of 5-10 mM at pH 6.0, while the stabilization effect increased with histidine concentration at pH 6.5 as shown by the results at 25-50 mM.

Figure 10:
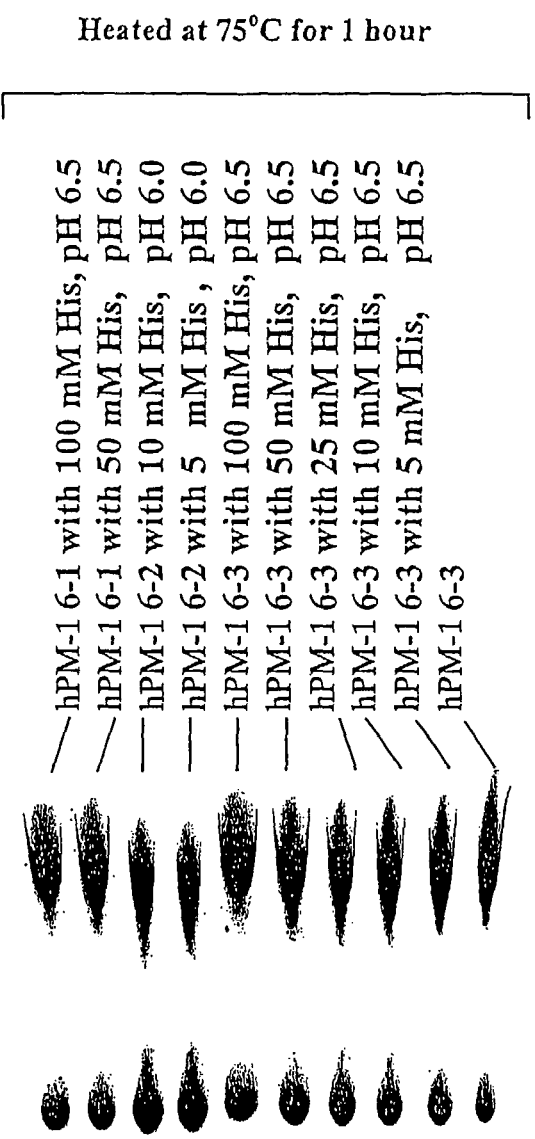
FIG. 10 shows the results of native gel analysis in which sample 6-1, pH 6.5, sample 6-2, pH 6.0 and sample 6-3, pH 6.5 were compared at various histidine concentrations (electrophoretogram).

Then, the effect of histidine concentration on aggregation was examined on other samples. FIG. 10 shows the results of comparison of sample 6-1, pH 6.5, sample 6-2, pH 6.0 and sample 6-3, pH 6.5 at various histidine concentrations.

Some stabilization effect was found in sample 6-3, pH 6.5 even when the concentration was increased to 100 mM, but the effect was greater at lower histidine concentrations such as 5-10 mM at pH 6.0 (sample 6-2) than every histidine concentration at pH 6.5. However, the actual histidine concentrations of sample 6-3 are 3.3 mM higher than indicated, because this sample initially contains 6.6 mM histidine.

Comparison of samples 6-1 and 6-3 at 50 or 100 mM (for the same reason, sample 6-3 here also contains histidine in an amount 3.3 mM higher than indicated) showed that sample 6-3 had a higher monomer content with less aggregation. Samples 6-1 and 6-3 differ in the means for adjusting the pH to 6.5. That is, sample 6-1 was adjusted to pH 6.5 with NaOH, while sample 6-3 was adjusted with concentrated histidine used as a base. Thus, stabilization effect is greater when histidine is used than when conventional NaOH is used to adjust the pH to 6.5.

Figure 11:
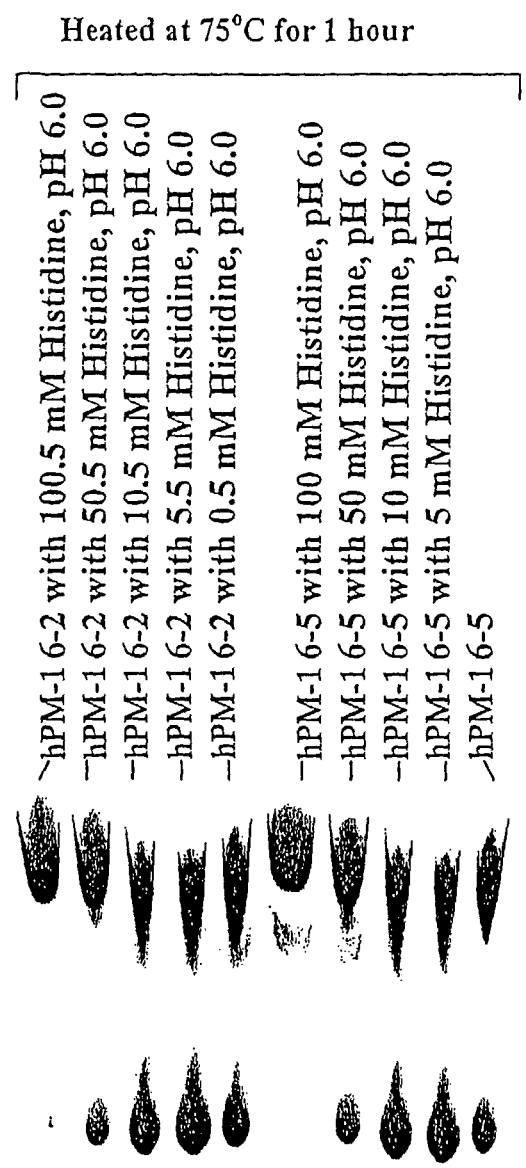
FIG. 11 shows the results of native gel analysis in which the effect of histidine was compared between two samples at pH 6.0, i.e. samples 6-2 and 6-5 (electrophoretogram).

FIG. 11 shows the results of comparison of the effect of histidine in two samples at pH 6.0, i.e. samples 6-2 and 6-5. In both samples, 5-10 mM histidine was the most effective.

Figure 12:
FIG. 12 shows the results of native gel analysis in which sample 6-1 (5 mM phosphate/Na, pH 6.5), sample 6-2 (5 mM phosphate/His, pH 6.0) and sample 6-5 (5 mM phosphate/Na, pH 6.0) were compared (electrophoretogram).

FIG. 12 shows the results of comparison of sample 6-1 (5 mM phosphate/Na, pH 6.5), sample 6-2 (5 mM phosphate/His, pH 6.0) and sample 6-5 (5 mM phosphate/Na, pH 6.0). The aggregate content was the lowest in 6-2 followed by 6-5 and then 6-1. This confirmed that antibody hPM-1 is more stable at pH 6.0. Samples 6-2 and 6-5 differ in the means for adjusting pH to 6.0. That is, sample 6-5 was adjusted to pH 6.0 with NaOH, while sample 6-2 was adjusted with concentrated histidine used as a base. Thus, stabilization effect is greater when histidine is used than when conventional NaOH is used to adjust the pH to 6.0 similarly to pH 6.5.

Figure 13:
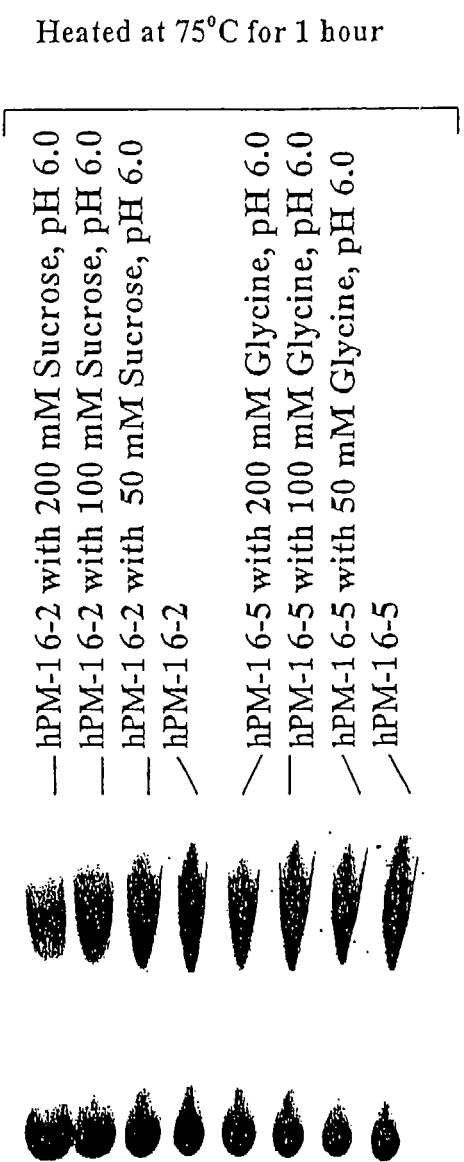
FIG. 13 shows the results of native gel analysis in which the effect of sucrose (50-200 mM) added to sample 6-2 and the effect of glycine (50-200 mM) added to sample 6-5 were compared (electrophoretogram).

FIG. 13 shows the effect of sucrose (50-200 mM) added to sample 6-2. Effective prevention of aggregation was observed as the sucrose concentration increased.

FIG. 13 also shows the effect of glycine (50-200 mM) added to sample 6-5. Remarkably effective prevention of aggregation was observed as the glycine concentration increased.

Figure 14:
FIG. 14 shows the results of native gel analysis in which the effect of 200 mM glycine or sucrose was compared in two samples at pH 6.0 (samples 6-2 and 6-5) (electrophoretogram).

FIG. 14 shows a comparison of the effect of 200 mM glycine or sucrose in two samples at pH 6.0 (6-2 and 6-5). Aggregation was less in 6-2 than 6-5. It was further confirmed from these results that pH adjustment is more effective with histidine than NaOH.

The invention claimed is:

1. A stabilized preparation comprising a humanized PM-1 (hPM-1) antibody in a histidine buffer, wherein the histidine buffer has a concentration of 5 mM to 20 mM, and wherein the stabilized preparation is a solution formulation, and which does not contain NaCl as an isotonizing agent, and which has a pH of 5.7-6.2, and wherein said preparation is free of sugar.

2. The stabilized preparation of claim 1, wherein said preparation comprises glycine as an isotonizing agent.

3. The stabilized preparation of claim 1, wherein histidine is the only buffering agent in said preparation.

4. A process for preparing a stabilized formulation comprising a humanized PM-1 (hPM-1) antibody, which comprises incorporating said antibody into a solution comprising a histidine buffer, in such manner as to result in a solution preparation having a pH of 5.7-6.2 and a histidine concentration of 5 mM to 20 mM, which preparation is free of sugar and does not contain NaCl as an isotonizing agent.

5. The process of claim 4, wherein histidine is the only buffering agent in said preparation.

6. The process of claim 4, comprising incorporating glycine as an isotonizing agent.

7. The process of claim 4, comprising adjusting the pH with a basic amino acid or a basic amino acid derivative or a salt thereof.

8. The process of claim 7, wherein the basic amino acid is one or more members selected from the group consisting of histidine, arginine and lysine.

9. The process of claim 8 wherein the basic amino acid is histidine.

\* \* \* \* \*

UNITED STATES PATENT AND TRADEMARK OFFICE
CERTIFICATE OF CORRECTION

| | | |
|---|---|---|
| PATENT NO. | : 8,632,778 B2 | Page 1 of 1 |
| APPLICATION NO. | : 10/380102 | |
| DATED | : January 21, 2014 | |
| INVENTOR(S) | : Masaya Kakuta | |

It is certified that error appears in the above-identified patent and that said Letters Patent is hereby corrected as shown below:

On the Title Page, item [54] and in the Specification, Column 1, Title, should read as follows:

-- STABILIZED ANTI-INTERLEUKIN-6 RECEPTOR ANTIBODY-CONTAINING PREPARATIONS --

Signed and Sealed this
Fifth Day of August, 2014

Michelle K. Lee
*Deputy Director of the United States Patent and Trademark Office*